(12) United States Patent
Van Antwerp et al.

(10) Patent No.: US 6,413,393 B1
(45) Date of Patent: Jul. 2, 2002

(54) SENSOR INCLUDING UV-ABSORBING POLYMER AND METHOD OF MANUFACTURE

(75) Inventors: William P. Van Antwerp, Valencia; John J. Mastrototaro, Los Angeles, both of CA (US)

(73) Assignee: MiniMed, Inc., Sylmar, CA (US)

( * ) Notice: Subject to any disclaimer, the term of this patent is extended or adjusted under 35 U.S.C. 154(b) by 0 days.

(21) Appl. No.: 09/348,771

(22) Filed: Jul. 7, 1999

(51) Int. Cl.[7] .................. G01N 27/26; G01N 27/00; G01N 35/00; C12Q 1/00; A61B 5/05

(52) U.S. Cl. .................. 204/403; 204/416; 204/418; 204/415; 356/32; 356/43; 356/51; 422/68.1; 422/50; 422/55; 422/61; 422/82.01; 422/82.05; 422/82.12; 422/82.13; 435/4; 435/287.1; 435/287.9; 436/43; 436/149; 436/164; 600/345

(58) Field of Search ................... 204/415, 418, 204/416, 403; 356/32–35.5, 39, 93–50, 51; 422/68.1, 50, 52, 55–62, 82.01–82.04, 82.05–82.13; 435/4, 287.1, 287.9; 436/43, 149, 150, 164, 165; 600/345, 347, 348, 354

(56) References Cited

U.S. PATENT DOCUMENTS

| | | | | |
|---|---|---|---|---|
| 4,840,919 A | * | 6/1989 | Attar | 436/111 |
| 5,182,624 A | * | 1/1993 | Tran et al. | 257/40 |
| 5,322,063 A | * | 6/1994 | Alen et al. | 600/347 |
| 5,798,031 A | * | 8/1998 | Charlton et al. | 204/403 |

OTHER PUBLICATIONS

CAPLUS abstract of Tarakanov et al. ("Photodegradation and photooxidative degradation of polyurethanes", J. Polym. Sci., Part C. (1968), vol. Date 1966, No. 23(Pt. 1), 193–9) month unknown.*

CAPLUS abstract of ("Phoacoustic study of UV, UV–thermal, and weathering degradation of rigid foam polyurethane", J. Appl. Polym. Sci. (1984), 29(8), 2443–52). Month unknown.*

\* cited by examiner

Primary Examiner—T. Tung
Assistant Examiner—Alex Noguerola
(74) Attorney, Agent, or Firm—Gates & Cooper LLP (57) ABSTRACT

A sensor is provided that includes at least one functional coating layer that includes a UV-absorbing polymer. Methods for making the inventive sensors are also provided.

51 Claims, 6 Drawing Sheets

SENSOR INCLUDING UV-ABSORBING POLYMER AND METHOD OF MANUFACTURE

FIELD OF THE INVENTION

The present invention relates to polymers having improved ultraviolet (UV) absorption, and to their use, in particular, in fabrication methods for producing thin film electrochemical sensors of the type used, for example, in subcutaneous or transcutaneous monitoring of blood glucose levels in a diabetic patient.

BACKGROUND OF THE INVENTION

Electrochemical sensors manufactured according to a variety of processes are known for use in a variety of specialized sensor applications. For example, electrochemical sensors manufactured using thin film processes are known. Such thin film sensors generally comprise one or more thin conductors applied by thin film deposition processes and subsequently patterned by photolithography mask and etch techniques between thin layers of a nonconductive film material, such as polyimide film. The conductors are shaped to define distal end sensor tips having an appropriate electrode material thereon, in combination with proximal end contact pads adapted for conductive connection with appropriate electronic monitoring equipment. In recent years, thin film sensors of this general type have been proposed for use as a transcutaneous sensor in medical applications. As one example, thin film sensors have been designed for use in monitoring blood glucose levels in a diabetic patient, with the distal end sensor electrodes positioned subcutaneously in direct contact with patient tissue.

In accordance with known photolithographic fabrication techniques, thin film sensors have been produced by sequential buildup of the sensor layers on a flat and rigid substrate, such as a glass plate. A base layer of insulative material is formed on the substrate, typically by applying the base layer material onto the substrate in liquid form and thereafter spinning the substrate to yield the base layer of thin, substantially uniform thickness. These steps are repeated to build up the base layer of sufficient thickness, followed by a sequence of photolithographic mask and etch steps to form the conductors. A cover layer of insulative material is then applied, and the resultant sensors are stripped from the substrate. However, this stripping step must be performed carefully in order to separate the finished sensors from the substrate without damage. Thus, the initial step of spin forming the base layer on the substrate must be carefully controlled so that the base layer that is firmly adhered to the substrate can be separated from the substrate at both reasonable cost and time, thereby increasing the efficiency and yield of the thin film sensors.

Subsequently, the remaining components of one or more thin film sensors are applied to the base layer, preferably by photolithographic mask and etch techniques. For example, a thin conductive film is applied to the base layer by electrodeposition, sputtering, etc. The conductive film is appropriately masked and etched to define elongated conductor traces for one or more sensors. The conductor traces are in turn covered by a thin film cover layer. The thus-formed sensors are removed from the substrate by cutting the cover and base layers along a line surrounding each finished sensor, whereupon each sensor can then be lifted and separated easily from the underlying substrate.

In particular thin film sensor fabrication techniques, the thin film cover layer is formed from a hydrophilic polyurethane and the base layer is formed from a polyimide, affording a polyurethane-polyimide laminate structure. One problem that characterizes such fabrication techniques is the substantial transparency of the polyurethanes that are used. Known polyurethanes are substantially transparent at the wavelength of the laser source (355 nm) typically used to cut the finished sensors from the laminate atop the substrate, although they do absorb UV at shorter wavelengths. (Shorter wavelength UV lasers are very expensive and not commonly employed.) On the other hand, the underlying polyimide layers do absorb in the 355 nm region. The underlying polyimide layer ablates after absorbing the UV radiation, and the overlying polyurethane layer is removed by the vaporized polyimide. The ablation process and subsequent expulsion of vaporized polyimide can cause delamination of the adjacent portions of the polyurethane layer from the polyimide layer.

A need exists for a sensor that includes a polymer, such as a polyurethane, that absorbs UV radiation, and for a method of making such a sensor. A more specific need exists for a sensor that includes a UV-absorbing polymer that absorbs UV radiation in substantially the same range as an underlying layer, such as a polyimide layer.

SUMMARY OF THE PREFERRED EMBODIMENTS

In accordance with one aspect of the present invention, there is provided a sensor including at least one functional coating layer. The functional coating layer includes a UV-absorbing polymer.

In a preferred embodiment, the UV-absorbing layer has a UV absorption of at least 0.3 AU based on a thickness of 4 mm at least one wavelength between 400 nm and 200 nm.

According to more specific embodiments, the UV-absorbing polymer is a polyurethane, a polyurea or a polyurethane/polyurea copolymer. More preferably, the selected UV-absorbing polymer is formed from a reaction mixture including a diisocyanate, at least one diol, diamine or mixture thereof, and a polyfunctional UV-absorbing monomer.

In another more specific embodiment, the sensor includes a base layer, a cover layer and a sensor element disposed between the base and cover layers. The cover layer has defined therein at least one opening above at least a portion of the sensor element.

Preferred embodiments of the inventive sensor are substantially planar or substantially cylindrical, and include base layers that are self-supportive or non-self-supportive.

According to a specific preferred embodiment, the sensor element is an electrically conductive sensor element. Preferably, an enzyme, such as glucose oxidase, is disposed in the opening defined above the sensor element. According to another specific preferred embodiment, the sensor element is a material that is chemically reactive with a preselected analyte whose presence is to be determined in a sample.

Two or more different materials can be used to form a plurality of sensor elements. Non-specifically reactive materials can also be used as control elements.

In accordance with another aspect of the present invention, a sensor is provided that includes a base layer, a sensor element disposed on the base layer, a cover layer that covers the sensor element and has defined therein at least one opening above at least a portion of the sensor element, and at least one functional coating layer. The functional coating layer includes a UV-absorbing polymer.

According to a more specific embodiment, the inventive sensor includes two or more functional coating layers, each of which includes a UV-absorbing polymer.

In preferred embodiments, the base and cover layers are made of an insulative material such as a polyimide.

In accordance with still another aspect of the present invention, there is provided a method of making a sensor including at least one functional coating layer. The method includes the step of forming the functional coating layer from a UV-absorbing polymer.

In accordance with yet another aspect of the present invention, a method of making a sensor includes the steps of forming a base layer, forming a sensor element on the base layer; forming a cover layer covering the sensor element and at least a portion of the base layer, defining at least one opening in the cover layer above at least a portion of the sensor element, and forming at least one functional coating layer on the cover layer. The functional coating layer includes a UV-absorbing polymer.

Sensors made according to the foregoing methods are also provided.

Other objects, features and advantages of the present invention will become apparent to those skilled in the art from the following detailed description. It is to be understood, however, that the detailed description and specific examples, while indicating preferred embodiments of the present invention, are given by way of illustration and not limitation. Many changes and modifications within the scope of the present invention may be made without departing from the spirit thereof, and the invention includes all such modifications.

BRIEF DESCRIPTION OF THE DRAWINGS

The invention may be more readily understood by referring to the accompanying drawings in which FIGS. 1–12 illustrate a particular method of the invention. In the drawings.

Like elements are numbered alike throughout the various figures.

DETAILED DESCRIPTION OF THE PREFERRED EMBODIMENTS

The present invention provides sensors that are readily processed using UV radiation, as well as methods for the production of the inventive sensors that facilitate size definition, interlayer definition, definition of active and inactive areas, and removal from the substrate on which they are prepared after processing is complete. Benefits afforded by various embodiments of the inventive sensors and methods for their production in addition include the solutions of manufacturing problems that characterize known production methods requiring the use of cutting lasers tuned to UV wavelengths.

As used herein, the term "functional coating layer" denotes a layer that coats at least a portion of at least one surface of a sensor, more preferably substantially all of a surface of the sensor, and that is capable of interacting with one or more analytes, such as chemical compounds, cells and fragments thereof, etc., in the environment in which the sensor is disposed. Non-limiting examples of functional coating layers include analyte limiting layers, i.e., layers that operate to prevent or restrict the diffusion of one or more analytes, such as glucose, through the layers; biocompatible layers; layers that increase the slipperiness of the sensor; layers that promote cellular attachment to the sensor; layers that reduce cellular attachment to the sensor; and the like. Functional coating layers do not include layers that merely permit the transmission of radiation In various embodiments of the present invention, the inventive sensor can be provided with one or more functional coating layers, which can be disposed one atop another, on different portions of the same surface of the sensor, on different surfaces of the sensor, etc.

According to the invention, any polymer that absorbs ultraviolet radiation can be used to form the functional coating layer. The functional coating layer can be comprised exclusively of the UV-absorbing polymer, or can include the UV-absorbing polymer as one ingredient of the functional coating layer (i.e., the functional coating layer can be comprised of a blend of polymers including at least one UV-absorbing polymer). In the latter case it is preferred that the layer formed from the resulting blend be sufficiently UV-absorbing to permit the layer to be cut using a source of UV radiation such as a laser.

For the purposes of this invention, a UV-absorbing polymer is a polymer that absorbs radiation in the region of the electromagnetic spectrum from 400 to 200 nm, , preferably 400 to 300 nm. Exemplary preferred UV-absorbing polymers strongly absorb UV at at least one ultraviolet wavelength (e.g., at 355 nm). For the purposes of the invention, a polymer "strongly absorbs UV" at a specific UV wavelength if a 4 mm thick membrane formed from the polymer has a UV absorption of at least about 0.3 Absorbance Unit (AU), more preferably 0.4 to 1.0 AU.

In a preferred embodiment, the UV-absorbing polymer absorbs UV at the same wavelength to which a laser, used to remove the sensor from the substrate, is tuned.

Preferred embodiments of the inventive sensor and method for its production employ UV-absorbing polymers that are biocompatible, i.e., polymers that are characterized by low cytotoxicity. Such polymers are particularly useful in fabricating sensors, in particular biosensors such as glucose sensors.

Examples of useful UV-absorbing polymers are described in co-pending U.S. patent application Ser. No. 09/349,270, (docket no. PD-0303), entitled "UV-Absorbing Polymer", filed simultaneously herewith and incorporated herein in its entirety by reference. The polymers described therein are formed from a reaction mixture including a diisocyanate, at least one selected from the group consisting of a diol, a diamine and mixtures thereof, and a polyfunctional UV-absorbing monomer. These polymers are polyurethanes, polyureas or polyurethane/polyurea copolymers that strongly absorb UV at 355 nm.

Useful diisocyanates for producing the foregoing exemplary polymers include, without limitation, those described in U.S. Pat. No. 5,786,439, to Van Antwerp et al., entitled "Hydrophilic, Swellable Coatings for Biosensors," which is incorporated herein in its entirety by reference. Such diisocyanates are typically used in the preparation of biocompatible polyurethanes (see in this regard gzycher, "Seminar on Advances in Medical Grade Polyurethanes," Technomic Publishing, (1995)) and include both aliphatic and aromatic diisocyanates. Suitable aliphatic diisocyanates include, for example, 4,4'-methylenebis(cyclohexylisocyanate) (H12MDI), 1,6-hexamethylene diisocyanate (HDI), trimethylhexamethylene diisocyanate (TMDI), trans-1,4-cyclohexane diisocyanate (CHDI), 1,4-cyclohexane bis(methylene isocyanate) (BDI), 1,3-cyclohexane bis(methylene isocyanate) (H6XDI), and isophorone diisocyanate (IPDI). Examples of suitable aromatic diisocyanates include toluene diisocyanate, 4,4'-diphenylmethane diisocyanate, 3,3'-dimethyl-4,4'-biphenyl diisocyanate, naphthalene diisocyanate and paraphenylene diisocyanate. In preferred embodiments, the diisocyanate is an aliphatic diisocyanate, more preferably 4,4'-methylenebis(cyclohexyl isocyanate), isophorone diisocyanate or 1,6-hexamethylene diisocyanate. A number of these diisocyanates are available from commercial sources such as Aldrich Chemical Company (Milwaukee, Wis., USA) or can be readily prepared by standard synthetic methods using literature procedures.

Figure 4:
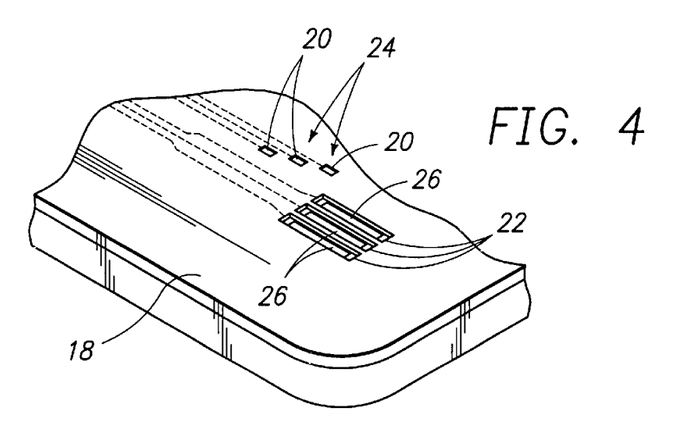
FIG. 4 is an enlarged fragmented perspective view illustrating sensor contact pad and distal end electrodes exposed through the insulative cover layer.

Diols that are useful in producing the foregoing exemplary polymers include, without limitation, poly(alkylene) glycols, polyester-based polyols, and polycarbonate polyols, such as those described in U.S. Pat. No. 5,777,060, to Van Antwerp, entitled "Silicon-Containing Biocompatible Membranes," which is incorporated herein in its entirety by reference. As used herein, the term "poly(alkylene)glycol" refers to polymers of lower alkylene glycols such as poly(ethylene)glycol, poly(propylene)glycol and polytetramethylene ether glycol (PTMEG). The term "polyester-based polyol" refers to a polymer as depicted in FIG. 4 of U.S. Pat. No. 5,777,060 in which the R group is a lower alkylene group such as ethylene, 1,3-propylene, 1,2-propylene, 1,4-butylene, 2,2-dimethyl-1,3-propylene, and the like. One of skill in the art will also understand that the diester portion of the polymer can also vary from the six-carbon diacid shown. For example, while FIG. 4 of U.S. Pat. No. 5,777,060 illustrates an adipic acid component, the present invention also contemplates the use of succinic acid esters, glutaric acid esters and the like. The term "polycarbonate polyol" refers those polymers having hydroxyl functionality at the chain termini and ether and carbonate functionality within the polymer chain. The alkyl portion of the polymer will typically be composed of $C_2$ to $C_4$ aliphatic radicals, or in some embodiments, longer chain aliphatic radicals, cycloaliphatic radicals or aromatic radicals.

Diamines that are useful in preparing the foregoing exemplary polymers include, without limitation, compounds corresponding to the foregoing diols in which the terminal hydroxyl groups have been replaced by reactive amine groups or in which the terminal hydroxyl groups have been derivatized to produce an extended chain having terminal amine groups. For example, a preferred hydrophilic diamine is a "diamino poly(oxyalkylene)" which is poly(alkylene) glycol in which the terminal hydroxyl groups are replaced with amino groups. The term "diamino poly(oxyalkylene)" also refers to poly(alkylene)glycols which have aminoalkyl ether groups at the chain termini. One example of a suitable diamino poly(oxyalkylene) is poly(propylene glycol)bis(2-aminopropyl ether). A number of the above polymers can be obtained from Aldrich Chemical Company. Alternatively, literature methods can be employed for their synthesis.

The foregoing exemplary polymers are produced using polyfinctional monomers that include UV absorbing moieties. As used here in, "polyfunctional" monomers include monomers having at least two functional groups that are reactive with isocyanates, i.e., difunctional or higher monomers. The foregoing exemplary polymers preferably include the UV absorbing moieties as pendent groups, but can also incorporate the UV absorbing moieties directly into the main chain of the polymers.

Preferably, the UV absorbing moieties are biocompatible, so that the resultant UV absorbing polymers can be used in the production of biosensors, in particular implantible biosensors, as well as other devices that come into contact with human and animal tissues and body fluids. However, non-biocompatible UV absorbers can also be used to produce polymers that are not intended for applications where biocompatibility is required.

Particularly preferred polyfunctional monomers having UV absorbing moieties include vitamin $B_2$ (riboflavin), which strongly absorbs UV in the range 266–371 nm, and vitamin $B_6$ (pyridoxine), which has broad UV absorption peaks at 255 nm, 291 nm and 326 nm. Both vitamin $B_2$ and vitamin $B_6$ are biocompatible and include a plurality of hydroxyl groups which are reactive with isocyanates. When vitamin $B_2$ is used, the UV-absorbing moiety is pendent from the main chain of the polymer. When vitamin $B_6$ is used, the UV-absorbing moiety is incorporated into the main chain of the polymer.

Additional biocompatible UV absorbers that are useful in the foregoing exemplary polymers include, without limitation, benzotriazole-based absorbers, such as 2,2'-dihydroxy-3-(2H-benzotriazol-2-yl)-3'-(4,6-diphenyl-s-triazin-2-yl)-5-methyl-6'-hexyloxy-diphenylmethane, 2,2'-dihydroxy-3-(2H-benzotriazol-2-yl)-3'-(4,6-diphenyi-s-triazin-2-yl)-5-tert-octyl-6'-hexyloxydiphenylmethane, etc., and benzophenone-based absorbers, such as 2-hydroxy-4-alkoxybenzophenone, 5,5'-methylene-bis(2-hydroxy-4-alkoxy-benzophenone) etc.

Useful non-biocompatible WV absorbers include, without limitation, copper phosphates, such as $6CuO.P_2O_5.3H_2O$, $Cu_3(PO_4)_2.3Cu(OH)_2$, $5CuO.P_2O_5.3H_2O$, $Cu_3(PO_4)_2.2Cu(OH)_2, H_2O$ $4CuO.P_2O_5$, $4CuO.P_2O_5.3H_2O$, $4CuO.P_2O_5.1.5H_2O$, $4CuO.P_2O_5.1.2H_2O$, and triazine compounds such as 2,4-bis[2-hydroxy-4-(2-hydroxyethoxy)-phenyl]-6-(4-chlorophenyl)-1,3,5-triazine, 2,4-bis(2,4-dihydroxyphenyl)-6-(4-chlorophenyl)-1,3,5-triazine, etc.

Combinations of two or more WV absorbing moieties are especially useful in affording a broadened range of UV absorption.

Figure 5:
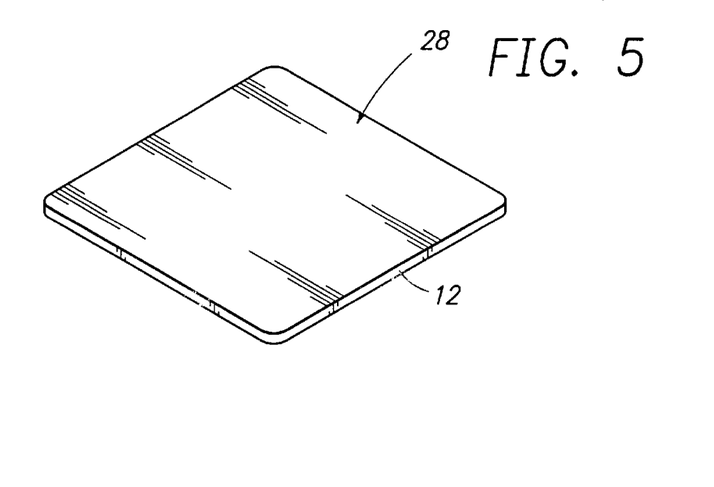
FIG. 5 is a perspective view illustrating the substrate.
Figure 6:
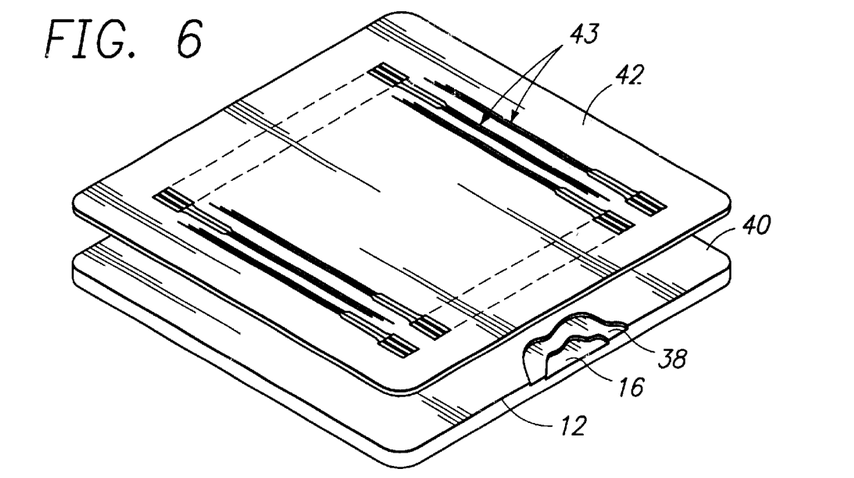
FIG. 6 is an exploded perspective view, with portions broken away, illustrating photolithographic mask and etch steps for forming conductive sensor traces on the base layer.
Figure 7:
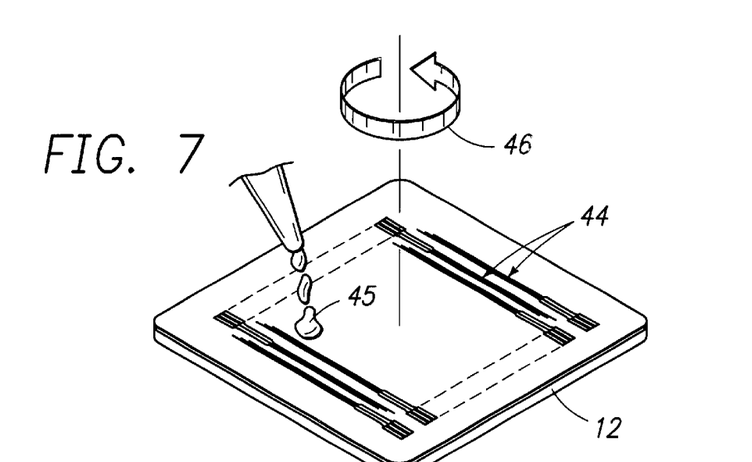
FIG. 7 is a perspective view illustrating application of a thin film cover layer over the conductive sensor traces.

Useful UV-absorbing polymers can also incorporate siloxane units. Siloxane units are incorporated by including in the reaction mixture one or more siloxane polymers having terminal functional groups, such as —OH or —NH$_2$. Exemplary siloxane polymers are described in U.S. Pat. No. 5,777,060, and include, polydimethylsiloxanes such as those illustrated in FIG. 5 therein. In some embodiments, combinations of silicone polymers can be used in which a first portion comprises hydroxyl groups and a second portion comprises amino groups. Preferably, the functional groups are positioned at the chain termini of the silicone polymers. A number of suitable silicone polymers are commercially available from such sources as Dow Chemical Company (Midland, Mich., USA) and General Electric Company (Silicones Division, Schenectady, N.Y., USA). Still others can be prepared by general synthetic methods as illustrated in FIGS. 6 and 7 of U.S. Pat. No. 5,777,060, beginning with commercially available siloxanes (United Chemical Technologies, Bristol. Pa., USA).

The molar ratio of diisocyanate:diol/diamine (with optional siloxane(s)) in the reaction mixture used to prepare the foregoing exemplary polymers preferably ranges from about 100:98 to about 100:90, more preferably 100:90 to 100:95. When a mixture of diols and diamines is used, preferably a smaller amount of diamines (which act as chain extenders) is used. The molar ratio of diols to diamines preferably ranges from about 90:10 to about 50:50, more preferably about 80:20 to about 60:40, very preferably about 70:30.

The amount of UV absorbing monomer(s) present in the foregoing exemplary polymers is preferably about 0.1 wt % to about 1.0 wt %, based on the non-volatile components of the reaction mixture, more preferably about 0.1 wt % to 0.3 wt %. A higher percentage results in greater cross-linking, yielding a stiffer and more brittle polymer.

Preferred embodiments of the inventive sensor include a base layer, a cover layer and at least one sensor element disposed between the base and cover layers. In more specific embodiments, at least one opening is defined above at least a portion of the sensor element. If desired, the exposed portion of the sensor element can then be provided with an appropriate electrode chemistry. For example, an enzyme such as glucose oxidase, glucose dehydrogenase or hexokinase, can be disposed on the exposed portion of the sensor element within the opening defined in the cover layer.

The sensor can have any desired configuration, for example planar or cylindrical. The base layer can be self-supportive, such as a rigid polymeric layer, or non-self supportive, such as a flexible film. The latter embodiment is desirable in that it permits continuous manufacture of sensors using, for example, a roll of a polymeric film which is continuously unwound and upon which sensor elements, cover layers and functional coating layers are continuously applied.

Useful sensor elements according to the present invention include thin film conductors or other electrically conductive elements that produce detectable electrical signals (referred to herein as conductive elements). Sensor elements are not limited to conductive elements, however. Other useful sensor elements can be formed from any material that is capable of producing a detectable non-electrical signal after interacting with a preselected analyte whose presence is to be detected (referred to herein as reactive elements). The detectable non-electrical signal can be, for example, an optically detectable change, such as a color change or a visible accumulation of the desired analyte (e.g., cells). Exemplary materials include polymers that bind specific types of cells; single-strand DNA; antigens; antibodies and reactive fragments thereof; etc. Sensor elements can also be formed from materials that are non-specifically reactive (i.e., controls). The foregoing alternative sensor elements are beneficially included, for example, in sensors for use in cell-sorting assays and assays for the presence of pathogenic organisms, such as viruses (HIV, hepatitis-C, etc.), bacteria, protozoa, etc.

If desired, a plurality of different sensor elements can be included in a single sensor. For example, both conductive and reactive sensor elements can be combined in one sensor, with each sensor element being disposed on a different portion of the base layer. One or more control elements can also be provided. In such embodiments, the inventive sensor has defined in its cover layer a plurality of openings.

One or more openings can also be defined in the cover layer directly over a portion of the base layer, in order to provide for interaction of the base layer with one or more analytes in the environment in which the sensor is disposed.

The base and cover layers can be comprised of a variety of materials, typically polymers. In more specific embodiments the base and cover layers are comprised of an insulative material such as a polyimide.

UV-absorbing polymers are used with advantage in a variety of sensor fabrication methods, such as those described in U.S. Pat. No. 5,390,671, to Lord et al., entitled "Transcutaneous Sensor Insertion Set"; No. 5,165,407, to Wilson et al., entitled "Implantable Glucose Sensor"; and U.S. Pat. No. 4,890,620, to Gough, entitled "Two-Dimensional Diffusion Glucose Substrate Sensing Electrode", which are incorporated herein in their entireties by reference. However, any sensor production method which includes the step of forming a UV-absorbing polymer layer over a sensor element is considered to be within the scope of the present invention. In particular, the inventive methods are not limited to thin-film fabrication methods, and can work with other sensor fabrication methods that utilize UV-laser cutting. Embodiments can work with thick-film, planar or cylindrical sensors and the like, and other sensor shapes requiring laser cutting.

Figures 1, 2:
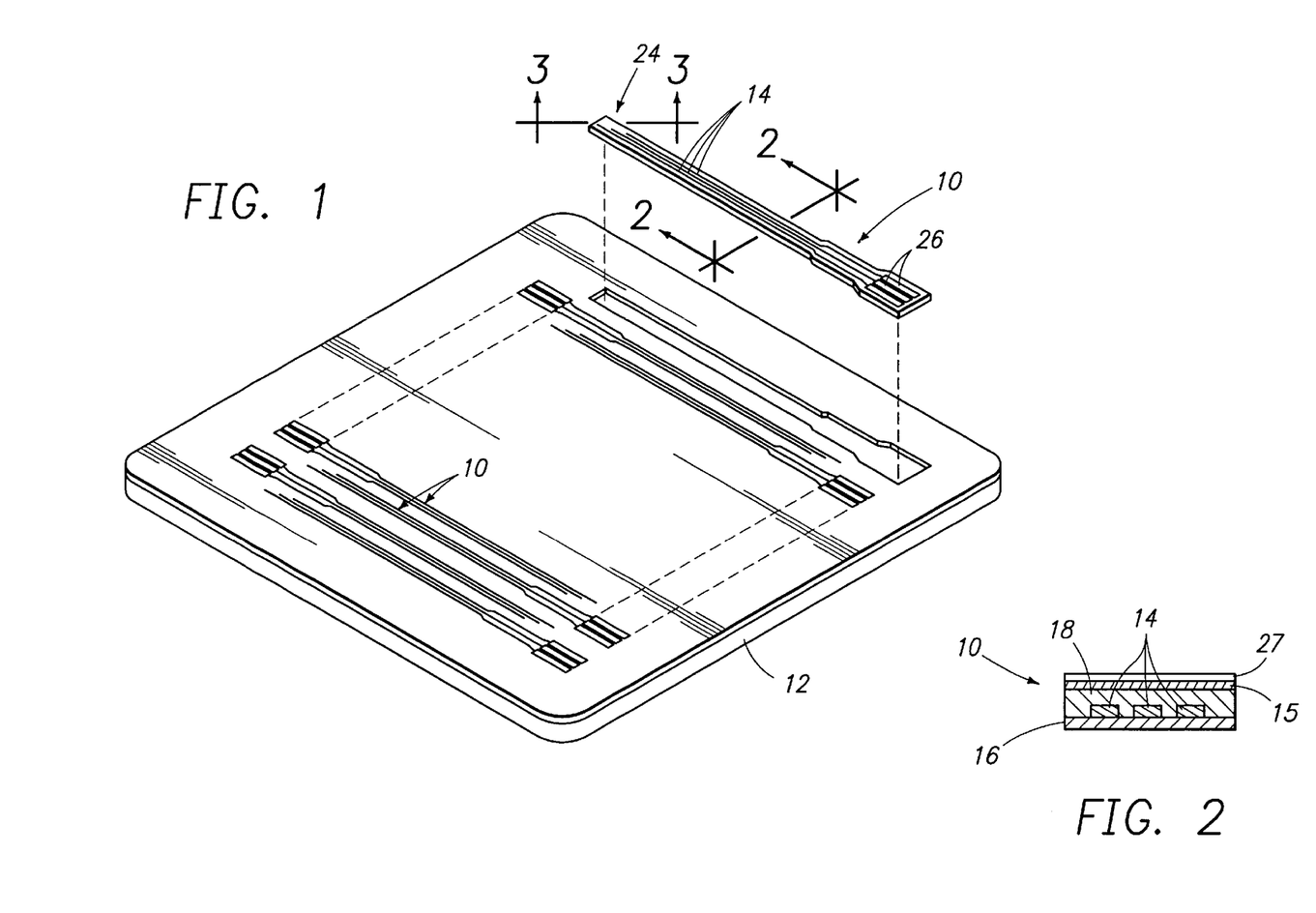
FIG. 1 is an exploded perspective view illustrating a plurality of thin film electrochemical sensors formed on a flat substrate according to a particular method of the invention.
FIG. 2 is an enlarged cross sectional view taken generally on the line 2—2, of FIG. 1.

An exemplary method according to the invention is shown in the figures. According to this method, as illustrated in FIG. 1, one or more sensors 10, for example thin film electrochemical sensors, are formed on a rigid flat substrate 12, such as a glass plate. The sensors 10 are formed in a manner which is compatible with photolithographic mask and etch techniques, but wherein the sensors are not physically adhered or attached directly to the substrate 12. Accordingly, finished sensors 10 can be removed quickly and easily from the substrate by simple lift-off separation, preferably after cutting using a laser tuned to a UV wavelength (e.g., 355 nm).

Figure 3:
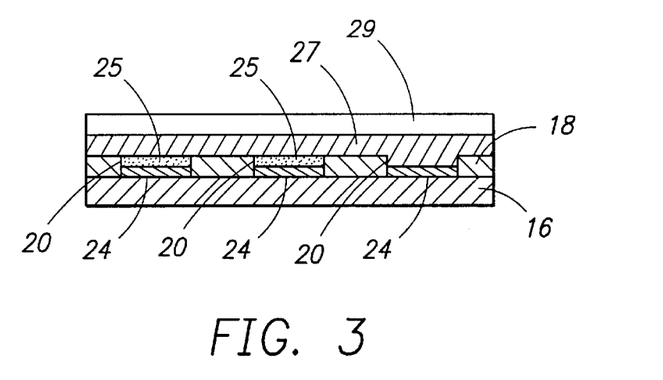
FIG. 3 is an enlarged cross sectional view taken generally on the line 3—3, of FIG. 1.

The sensors 10 shown in the accompanying drawings are particularly designed for use as subcutaneous or transcutaneous glucose sensors for monitoring blood glucose levels in a diabetic patient. Each sensor 10 comprises a plurality of sensor elements 14, for example electrically conductive elements such as elongated thin film conductors, formed between an underlying insulative thin film base layer 16 (FIGS. 2–3) and an overlying insulative thin film cover layer 18. On cover layer 18 one or more functional coating layers are formed from a UV-absorbing polymer as described above. Two functional coating layers are illustrated, an analyte limiting layer 27 which limits the diffusion of glucose, and a biocompatible layer 29.

Openings 20 and 22 (FIG. 4) are formed in the cover layer 18 to expose distal end electrodes 24 and proximal end contact pads 26. In a glucose monitoring application, for example, the sensor 10 is placed transcutaneously so that the distal end electrodes 24 are in contact with patient blood or extracellular fluid, and the contact pads 26 are disposed externally for convenient connection to a monitoring device (not shown).

In certain embodiments, the substrate 12 comprises a rigid and flat structure suitable for use in photolithographic mask and etch processes. In this regard, the substrate 12 defines an upper surface 28 (FIG. 5) having a high degree of uniform flatness. A polished glass plate may be used defining the smooth upper surface 28. Alternative substrate materials include, for example, stainless steel, aluminum, and plastic materials such as delrin, etc. In other embodiments, the substrate is non-rigid and can be another layer of film or insulation that is used as a substrate, for example plastics such as polyimides and the like.

The base layer 16 can be secured to the substrate 12 by any desired means, for example by use of an adhesive applied about the perimeter of the substrate 12 followed by subsequent curing. Alternatively, controlled spin coating can be used. In addition, an adhesive can be omitted if sufficient adhesion between the substrate 12 and the base layer is produced.

FIG. 6 illustrates photolithographic steps for forming conductive sensor traces on the base layer 16 in accordance with an exemplary embodiment of the inventive method. More specifically, the base layer 16 is initially coated with a thin film conductive layer 38 by electrode deposition, surface sputtering, or other suitable process step. In the preferred form, this conductive layer 38 may be provided as a plurality of thin film conductive layers, such as an initial chrome-based layer suitable for chemical adhesion to a polyimide base layer 16, followed by subsequent formation of thin film gold-based and chrome-based layers in sequence.

In alternative embodiments, other electrode layer conformations or materials can be used.

The conductive layer 38 is then covered, in accordance with conventional photolithographic techniques, with a selected photoresist coating 40, and a contact mask 42 is applied over the photoresist coating 40 for suitable photo-imaging. The contact mask includes one or more conductor trace patterns 43, such as the plurality of traces shown in FIG. 6 in closely nested relation, for appropriate exposure of the photoresist coating 40, followed by an etch step resulting in a plurality of conductive sensor traces 44 remaining on the base layer 16, as shown in FIG. 7. In the illustrative sensor construction designed for use as a subcutaneous glucose sensor, each sensor trace is shown to include three parallel sensor elements 14 corresponding with three separate electrodes 24 as will be described.

Figure 8:
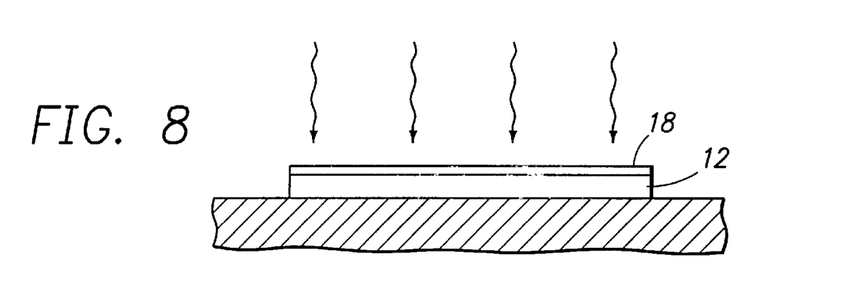
FIG. 8 is a schematic representation of a cure step for curing the cover layer.

The conductive sensor traces 44 are covered by the thin film cover layer 18, preferably of an insulative material such as a polyimide. The cover layer 18 can be applied in any desired manner. In an exemplary procedure, the cover layer is applied in a liquid layer 45 over the sensor traces 44, after which the substrate 12 is spun as indicated by arrow 46 to distribute the liquid material 45 as a thin film overlying the sensor traces 44 and extending beyond the marginal edges of the sensor traces in sealed contact with the base layer. This liquid material is then subjected to a suitable radiation and/or heat cure step as shown in FIG. 8.

In alternative embodiments, the liquid material 45 can be applied using spray techniques or any other desired means of application.

Figure 9:
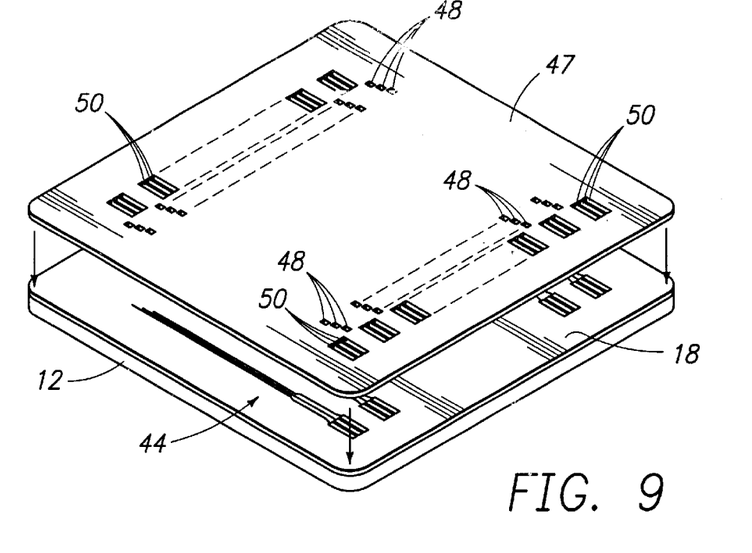
FIG. 9 is an exploded perspective view illustrating photoimaging steps for exposing portions of the conductive sensor traces.

FIG. 9 shows a contact mask 47 for placement over the cured cover layer 18. The contact mask 47 has apertures 48 and 50 formed therein through which the photoimagable layer 18 can be exposed to an appropriate light source. The thus-exposed cover layer 18 is subsequently processed to remove portions of the cover layer 18, resulting in the openings 20 and 22 (FIG. 4) which respectively expose the distal end sensor tips and proximal end contact pads 26 of each sensor trace.

Appropriate electrode chemistries defining the distal end electrodes 24 can be applied to the sensor tips subsequent to exposure of the sensor tips through the openings 20, or alternately before application of the cover layer 18. In this illustrative sensor embodiment for use as a glucose sensor, an enzyme 25 (here, glucose oxidase) is provided within one of the openings 20, thus coating one of the sensor tips to define a working electrode. The other two electrodes 24 can be provided with other suitable chemistries, such as other enzymes (a second enzyme is shown), left uncoated, or provided with chemistries to define a reference electrode and a counter electrode for the electrochemical sensor.

Figure 10:
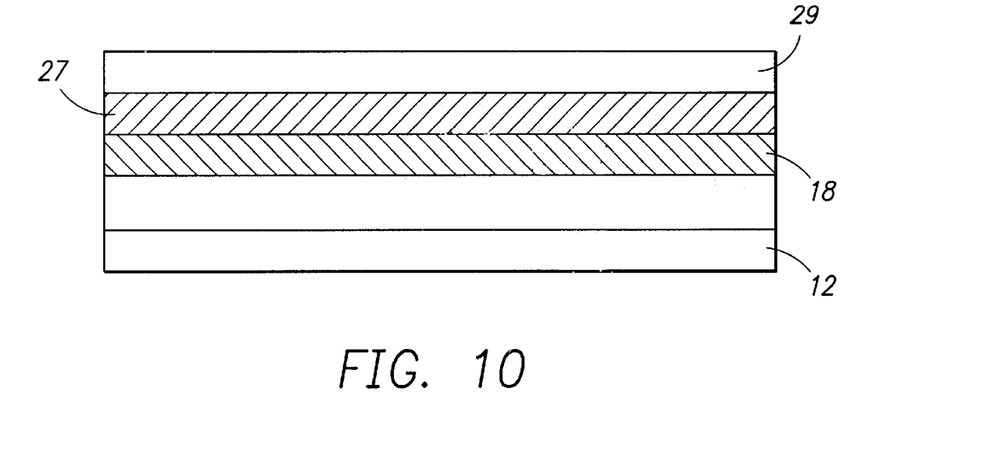
FIG. 10 is a schematic representation of steps for application of functional coating layers.

Subsequent to treatment of the tips of the sensor elements, one or more functional coating layers are then applied by any desired method, such as spraying, dipping, etc. As shown in FIG. 10, two functional coating layers 27 and 29 are provided.

Figure 11:
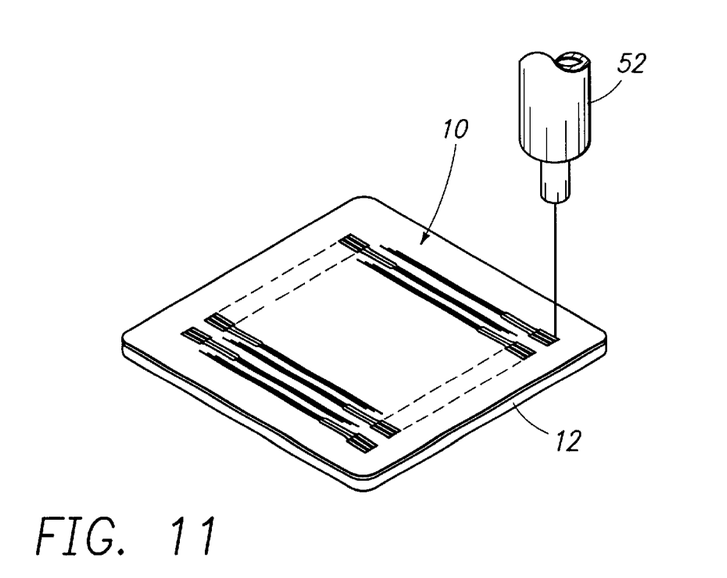
FIG. 11 is a perspective view illustrating removal of each finished sensor from the substrate.

The finished sensors 10 are quickly and easily removed from the substrate 12 by cutting along a line 11 surrounding each sensor on the substrate. FIG. 11 shows the cutting step to include a UV laser cutting device 52 used to cut through the base and cover layers 16, 18 and the functional coating layers 27, 29 along a line surrounding or circumscribing each sensor, typically in at least slight outward spaced relation from the conductive elements so that the sufficient interconnected base and cover layer material remains to seal the side edges of the finished sensor. Since the base layer 16 is not physically attached or only minimally adhered directly to the underlying substrate 12, the sensors 10 can be lifted quickly and easily from the substrate, without significant further processing steps or potential damage due to stresses incurred by physically pulling or peeling attached sensors from the substrate. The substrate 12 can thereafter be cleaned and reused, or otherwise discarded.

Alternatively, the functional coating layer(s) can be applied after the sensor including base layer 16, sensor elements 14 and cover layer 18 is removed from the substrate by cutting.

Figure 12:
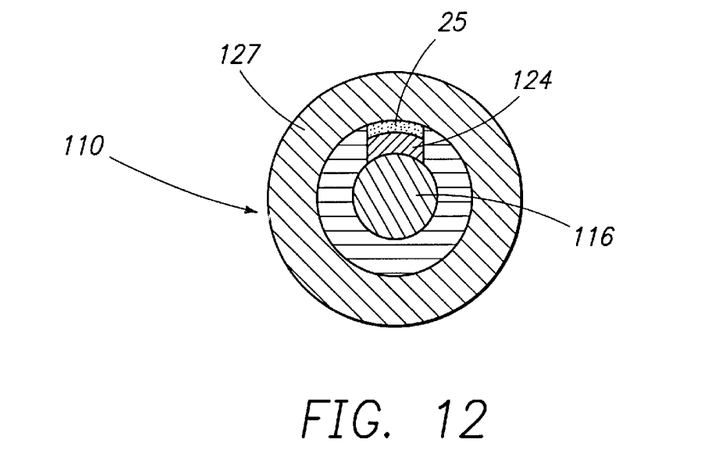
FIG. 12 is a sectional view of an alternative cylindrical embodiment of a sensor according to the invention.

As shown in FIG. 12, an alternative substantially cylindrical sensor 12 includes a cylindrical base layer 116 and a cover layer 118, between which is disposed a sensor element having an end 124. An opening 120 is defined through cover layer 118 above the end 124 of the sensor element, and an enzyme is provided within the opening. A functional coating layer 127 as described herein in turn surrounds the base and cover layers, the sensor element and the enzyme.

Typically these sensors are formed by photoresist, etching and rinsing to define the geometry of the active electrodes. The electrodes are then made electrochemically active typically by electrodeposition of Pt black for the working and counter electrode, and silver followed by silver chloride on the reference electrode. The enzyme is then deposited by electrochemical deposition, dipping, spraying, microdroplet deposition or other techniques, followed by crosslinking with either a dialdehyde (glutaraldehyde) or with a carbodi-imide.

Figure 13:
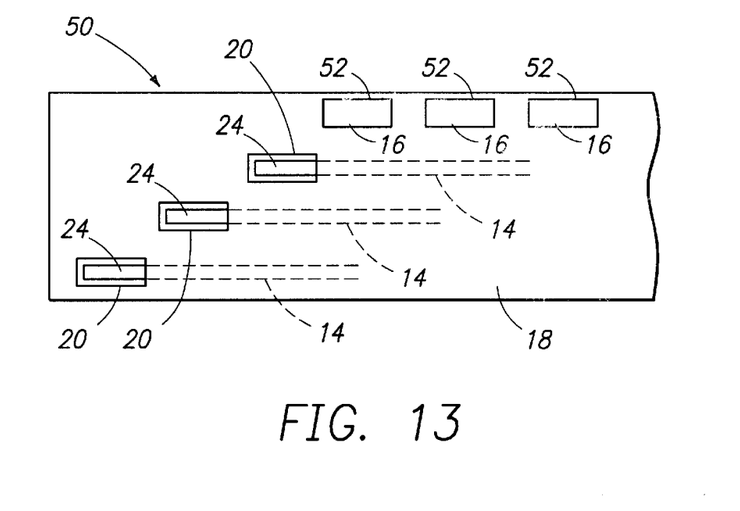
FIG. 13 is a top plan view of an alternative embodiment of a portion of a sensor including both conductive and reactive sensor elements.
Figure 14:
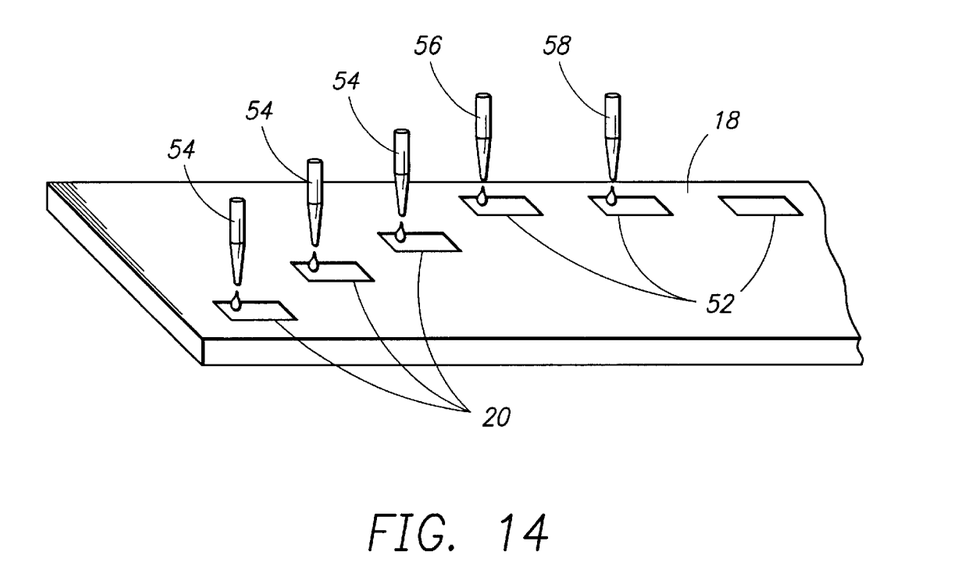
FIG. 14 is a side perspective view illustrating formation of the conductive and reactive sensor elements of the embodiment of FIG. 13.

FIGS. 13 and 14 illustrate an alternate embodiment which combines conductive and reactive sensor elements in a single sensor. In FIG. 13, sensor 50 includes sensor elements 14 having distal ends 24 above which openings 20 are formed in cover layer 18 as in the preceding embodiment. One or more additional openings 52 (three are illustrated) are also formed through cover layer 18 to facilitate formation of reactive sensor elements. In FIG. 14, one or more electrode chemistries, for example one or more enzymes, are provided in openings 20 by injectors 54 to form conductive sensor elements. At the same time, one or more reactive sensor elements are formed in openings 52. For example, a solution of single-strand DNA from a pathogenic organism, such as HIV, can be dispensed via injector 56 into a first opening 52, while a solution of an anti-HIV immunoglobulin can be dispensed via injector 58 into a second opening 52. The third opening 52 can be left unfilled in order to allow analyte access to the base layer 16. Once the various solutions have dried, one or more functional coating layers are then applied by any desired means. Further processing, for example according to the method described above, affords a completed sensor.

While the description above refers to particular embodiments of the present invention, it will be understood that many modifications may be made without departing from the spirit thereof. The accompanying claims are intended to cover such modifications as would fall within the true scope and spirit of the present invention.

The presently disclosed embodiments are therefore to be considered in all respects as illustrative and not restrictive, the scope of the invention being indicated by the appended claims, rather than the foregoing description, and all changes which come within the meaning and range of equivalency of the claims are therefore intended to be embraced therein.

What is claimed is:

1. An implantable sensor comprising at least one functional coating layer, wherein the functional coating layer includes a UV-absorbing polymer and is biocompatible with human and animal tissue and fluids surrounding the human and animal tissue; and wherein the UV-absorbing polymer absorbs radiation in substantially the same range as an underlying layer.

2. The sensor of claim 1 wherein said UV-absorbing polymer is a polyurethane, a polyurea, a polyurethane/polyurea copolymer, polymethacrylate, polyacrylic acid, polycarbonate, or mixtures of these polymers.

3. The sensor of claim 1 wherein said functional coating layer is selected from the group consisting of an analyte limiting layer, a layer that increases the slipperiness of said sensor, a layer that promotes cellular attachment to said sensor and a layer that reduces cellular attachment to said sensor.

4. The sensor of claim 1, wherein the UV-absorbing polymer is biocompatible with human and animal tissue.

5. A sensor comprising at least one functional coating layer, wherein said functional coating layer comprises a UV-absorbing polymer selected from at least a polyurethane, a polyurea, a polyurethane/polyurea copolymer, polymethacrylate, polyacrylic acid, polycarbonate, and mixtures of these polymers and wherein said polymer is formed from a reaction mixture comprising a diisocyanate, at least one selected from the group consisting of a diol, a diamine and mixtures thereof, and a polyfunctional UV-absorbing monomer.

6. A sensor comprising a plurality of functional coating layers each of which comprises a UV-absorbing polymer.

7. A sensor comprising at least one functional coating layer, wherein said functional coating layer comprises a UV-absorbing polymer, the sensor being substantially planar and further including a base layer, a cover layer and a sensor element disposed between said base and cover layers, wherein said cover layer has defined therein at least one opening above at least a portion of said sensor element and said base layer is comprised of a flexible material; and wherein the UV-absorbing polymer absorbs radiation in substantially the same range as an underlying layer.

8. A sensor comprising at least one functional coating layer, wherein said functional coating layer comprises a UV-absorbing polymer, the sensor being substantially cylindrical and further including a base layer, a cover layer and a sensor element disposed between said base and cover layers, wherein said cover layer has defined therein at least one opening above at least a portion of said sensor element and said base layer is comprised of a flexible material; and wherein the UV-absorbing polymer absorbs radiation in substantially the same range as an underlying layer.

9. A sensor comprising at least one functional coating layer, wherein said functional coating layer comprises a UV-absorbing polymer, the sensor further including a base layer, a cover layer and a conductive sensor element disposed between the base and cover layers, wherein the cover layer has defined therein at least one opening above at least a portion of the sensor element and wherein an enzyme is disposed in said opening; and wherein the UV-absorbing polymer absorbs radiation in substantially the same range as an underlying layer.

10. The sensor of claims 9 wherein said enzyme is selected from the group consisting of glucose oxidase, glucose dehydrogenase, lactose oxidase, hexokinase, lactose dehydrogenase.

11. The sensor of claim 10 wherein said enzyme is glucose oxidase.

12. A sensor comprising at least one functional coating layer, wherein said functional coating layer comprises a UV-absorbing polymer, the sensor further including a base layer, a cover layer and a sensor element disposed between the base and cover layers, wherein said cover layer has defined therein a plurality of openings with at least one opening being above at least a portion of the sensor element; and wherein the UV-absorbing polymer absorbs radiation in substantially the same range as an underlying layer.

13. The sensor of claim 12 comprising a plurality of sensor elements, wherein at least one said opening is defined above at least a portion of each of said plurality of sensor elements.

14. The sensor of claim 13 wherein said plurality of sensor elements comprise at least two materials that are reactive with different preselected analytes.

15. The sensor of claim 12 further comprising a control sensor element including non-specifically reactive materials.

16. A sensor comprising:
  a) a base layer,
  b) a sensor element disposed on said base layer,
  c) a cover layer covering said sensor element and having defined therein at least one opening above at least a portion of said sensor element, and
  d) at least one functional coating layer, wherein said functional coating layer comprises a UV-absorbing polymer and is biocompatible; and wherein the UV-absorbing polymer absorbs radiation in substantially the same range as an underlying layer.

17. The sensor of claim 16 wherein said base layer is comprised of an insulative material.

18. A sensor comprising:
  a) a base layer,
  b) a sensor element disposed on said base layer,
  c) a cover layer covering said sensor element and having defined therein at least one opening above at least a portion of said sensor element, and
  d) at least functional coating layer wherein said functional coating layer comprise a UV-absorbing polymer and is a polyurethane, a polyurea or a polyurethane/polyurea copolymer; and wherein the UV-absorbing polymer absorbs radiation in substantially the same range as an underlying layer.

19. A sensor comprising:
  a) a base layer,
  b) a sensor element disposed on said base layer,
  c) a cover layer covering said sensor element and having defined therein at least one opening above at least a portion of said sensor element, and
  d) at least functional coating layer wherein said functional coating layer comprise a UV-absorbing polymer having a UV absorption of at least 0.3 AU based on a thickness of 4 mm at at least one wavelength between 400 nm and 100 nm; and wherein the UV-absorbing polymer absorbs radiation in substantially the same range as an underlying layer.

20. The sensor of claim 19 wherein said wavelength is 355 nm.

21. A sensor comprising:
  a) a base layer,
  b) a sensor element disposed on said base layer,
  c) a cover layer covering said sensor element and having defined therein at least one opening above at least a portion of said sensor element, and d) at least functional coating layer wherein said functional coating layer comprise a UV-absorbing polymer formed from a reaction mixture comprising a diisocyanate, at least one selected from the group consisting of a diol, a diamine and mixtures thereof, and a polyfunctional UV-absorbing monomer.

22. A sensor comprising:
a) a base layer,
b) a sensor element disposed on said base layer,
c) a cover layer covering said sensor element and having defined therein at least one opening above at least a portion of said sensor element, and
d) at least one functional coating layer, wherein said functional coaring layer comprises a UV-absorbing polymer and is selected from the group consisting of an analyte limiting layer, a biocompatible layer, a layer that increases the slipperiness of said sensor, a layer that promotes cellular attachment to said sensor and a layer that reduces cellular attachment to said sensor; and wherein the UV-absorbing polymer absorbs radiation in substantially the same range as an underlying layer.

23. A sensor comprising:
a) a base layer,
b) a sensor element disposed on said base layer,
c) a cover layer covering said sensor element and having defined therein at least one opening above at least a portion of said sensor element, and
d) at least two functional coating layers, each of which comprises a UV-absorbing polymer.

24. A sensor comprising:
a) a base layer comprised of a polyimide,
b) a sensor element disposed on said base layer,
c) a cover layer coveting said sensor element and having defined therein at least one opening above at least a portion of said sensor element, and
d) at least two functional coating layers wherein said functional coating layers comprise a UV-absorbing polymer.

25. A sensor comprising:
a) a base layer,
b) a sensor element disposed on said base layer,
c) a cover layer covering said sensor element and having defined therein at least one opening above at least a portion of said sensor element, and
d) at least two functional coating layers wherein said functional coating layers comprise a UV-absorbing polymer, wherein said cover layer is comprised of an insulative material.

26. A sensor comprising:
a) a base layer comprised of a polyimide,
b) a sensor element disposed on said base layer,
c) a cover layer comprised of an insulative material and covering said sensor element and having defined therein at least one opening above at least a portion of said sensor element, and
d) at least two functional coating layers wherein said functional coating layers comprise a UV-absorbing polymer.

27. A method of making a sensor comprising forming a functional coating layer from a UV-absorbing polymer, wherein the UV-absorbing polymer is biocompatible; and wherein the UV-absorbing polymer absorbs radiation in substantially the same range as an underlying layer.

28. The method of claim 27, wherein said UV-absorbing polymer is a polyurethane, a polyurea or a polyurethane/polyurea copolymer.

29. The method of claim 27 wherein said functional coating layer is selected from the group consisting of an analyte limiting layer, a layer that increases the slipperiness of said sensor, a layer that promotes cellular attachment to said sensor and a layer that reduces cellular attachment to said sensor.

30. A method of making a sensor comprising forming at least two functional coating layers, each of said coating layers being formed from a UV-absorbing polymer.

31. A method of making a sensor comprising:
a) forming a base layer;
b) forming a sensor element on the base layer;
c) forming a cover layer covering the sensor element and at least a portion of the base layer;
d) defining at least one opening in the cover layer above at least a portion of the sensor element; and
e) forming a least one functional coating layer on the cover layer, wherein the functional coating layer includes a UV-absorbing polymer and is biocompatible; and wherein the UV-absorbing polymer absorbs radiation in substantially the same range as an underlying layer.

32. A sensor made by the method of claim 31.

33. A method of making a sensor comprising the steps of:
a) forming a base layer,
b) forming a sensor element on said base layer,
c) forming a cover layer covering said sensor element and at least a portion of said base layer,
d) defining at least one opening in said cover layer above at least a portion of said sensor element, and
e) forming at least one functional coating layer on said cover layer, said functional coating layer comprising UV-absorbing polymer, wherein said UV-absorbing polymer is a polyurethane, a polyurea or a polyurethane/polyurea copolymer; and wherein the UV-absorbing polymer absorbs radiation in substantially the same range as an underlying layer.

34. A method of making a sensor comprising the steps of:
a) forming a base layer,
b) forming a sensor element on said base layer,
c) forming a cover layer covering said sensor element and at least a portion of said base layer,
d) defining at least one opening in said cover layer above at least a portion of said sensor element, and
e) forming at least one functional coating layer on said cover layer, said functional coating layer comprising UV-absorbing polymer, wherein said UV-absorbing polymer has a UV-absorption of at least 0.3 AU based on a thickness of 4 mm at at least one wavelength between 400 nm and 100 nm; and wherein the UV-absorbing polymer absorbs radiation in substantially the same range as an underlying layer.

35. The method of claim 34 wherein said wavelength is 355 nm.

36. A method of making a sensor comprising the steps of:
a) forming a base layer,
b) forming a sensor element on said base layer,
c) forming a cover layer covering said sensor element and at least a portion of said base layer,
d) defining at least one opening in said cover layer above at least a portion of said sensor element, and
e) forming at least one functional coating layer on said cover layer, said functional coating layer comprising UV-absorbing polymer, wherein said UV-absorbing polymer is formed from a reaction mixture comprising a diisocyanate, at least one selected from the group consisting of a diol, a diamine and mixtures thereof, and a polyfunctional UV-absorbing monomer.

37. A method of making a sensor comprising the steps of:
a) forming a base layer,
b) forming a sensor element on said base layer,
c) forming a cover layer covering said sensor element and at least a portion of said base layer,
d) defining at least one opening in said cover layer above at least a portion of said sensor element, and
e) forming at least one functional coating layer on said cover layer, said functional coating layer comprising UV-absorbing polymer, wherein said functional coating layer is selected from the group consisting of an analyte limiting layer, a biocompatible layer, a layer that increases the slipperiness of said sensor, a layer that promotes cellular attachment to said sensor and a layer that reduces cellular attachment to said sensor; and wherein the UV-absorbing polymer absorbs radiation in substantially the same range as an underlying layer.

38. A method of making a sensor comprising the steps of:
a) forming a base layer,
b) forming a sensor element on said base layer,
c) forming a cover layer covering said sensor element and at least a portion of said base layer,
d) defining at least one opening in said cover layer above at least a portion of said sensor element, and
e) forming at least two functional coating layers on said cover layer, said at least two functional coating layers comprising a UV-absorbing polymer.

39. A method of making a sensor comprising the steps of:
a) forming a base layer,
b) forming a sensor element on said base layer,
c) forming a cover layer covering said sensor element and at least a portion of said base layer,
d) defining at least one opening in said cover layer above at least a portion of said sensor element, and
e) forming at least one functional coating layers on said cover layer, said functional coating layer comprising UV-absorbing polymer, wherein said sensor element is a conductive sensor element that is formed on said base layer; and wherein the UV-absorbing polymer absorbs radiation in substantially the same range as an underlying layer.

40. A method of making a sensor comprising the steps of:
a) forming a base layer,
b) forming a sensor element on said base layer,
c) forming a cover layer covering said sensor element and at least a portion of said base layer,
d) defining at least one opening in said cover layer above at least a portion of said sensor element, and
e) forming at least one functional coating layer on said cover layer, said functional coating layer comprising a UV-absorbing polymer, wherein said sensor element is formed by depositing on said base layer at least one material that is reactive with a preselected analyte; and wherein the UV-absorbing polymer absorbs radiation in substantially the same range as an underlying layer.

41. A method of making a sensor comprising the steps of:
a) forming a base layer,
b) forming a sensor element on said base layer,
c) forming a cover layer covering said sensor element and at least a portion of said base layer,
d) defining at least one opening in said cover layer above at least a portion of said sensor element, and
e) forming at least one functional coating layer on said cover layer, said functional coating layer comprising a UV-absorbing polymer, wherein at least two sensor elements are formed on said base layer prior to forming said cover layer; and wherein the UV-absorbing polymer absorbs radiation in substantially the same range as an underlying layer.

42. The method of claim 41 wherein the at least two sensor elements comprise at least two materials that are reactive with different preselected analytes.

43. The method of claim 41 wherein at least two openings are defined in said cover layer, at least one said opening being defined above at least a portion of each of said plurality of sensor elements.

44. The method of claim 41 wherein a second sensor element, which is a-control sensor element formed from non-specifically reactive materials, is disposed on said base layer prior to forming said cover layer.

45. A sensor comprising a base layer and at least one functional coating layer over at least a portion of the base layer, wherein said functional coating layer comprises a UV-absorbing polymer that absorbs radiation in substantially the same range as the base layer.

46. The sensor of claim 45 wherein said UV-absorbing polymer has a UV absorption of at least 0.3 AU based on a thickness of 4 mm at least one wavelength between 400 nm and 200 nm.

47. The sensor of claim 46 wherein the functional coating layer and the base layer absorb radiation at approximately 355 nm.

48. The sensor of claim 45 wherein said UV-absorbing polymer is biocompatible.

49. The sensor of claim 48 wherein the sensor is in contact with human or animal tissue.

50. The sensor of claim 45 wherein the UV-absorbing polymer is a polyurethane, a polyurea, a polyurethane/polyurea copolymer, polymethacrylate, polyacrylic acid, polycarbonate, or mixtures of these polymers.

51. The sensor of claim 45 wherein the functional coating layer is selected from at least an analyte limiting layer, a biocompatible layer, a layer that increases the slipperiness of the sensor, a layer that promotes cellular attachment to the sensor and a layer that reduces cellular attachment to the sensor.

* * * * *